United States Patent

Landis et al.

[11] Patent Number: 5,657,752
[45] Date of Patent: *Aug. 19, 1997

[54] NASAL POSITIVE AIRWAY PRESSURE MASK AND METHOD

[75] Inventors: Robert M. Landis, Mountainside; Wayne W. Disanza, Toms River, both of N.J.

[73] Assignee: Airways Associates, Matawan, N.J.

[*] Notice: The portion of the term of this patent subsequent to Nov. 19, 2013, has been disclaimed.

[21] Appl. No.: 621,709

[22] Filed: Mar. 28, 1996

[51] Int. Cl.⁶ .................................................. A62B 9/02
[52] U.S. Cl. ................... 128/207.13; 128/201.18; 128/204.18; 128/205.24; 128/206.18; 128/207.12
[58] Field of Search ............................. 28/201.18, 204.18, 28/205.24, 206.16, 206.18, 207.12, 207.16, 205.11, 207.13, 207.18

[56] References Cited

U.S. PATENT DOCUMENTS

| Re. 32,553 | 12/1987 | Bennett et al. | 128/204.18 |
| 812,706 | 2/1906 | Warbasse | 128/207.13 |
| 1,158,780 | 11/1915 | Bolton | 128/207.13 |
| 1,176,886 | 3/1916 | Ermold | 128/207.13 |
| 1,206,045 | 11/1916 | Smith | 128/207.13 |

(List continued on next page.)

FOREIGN PATENT DOCUMENTS

| 4010975 | 10/1991 | Germany | A61M 29/02 |
| 220978 | 6/1968 | Sweden | 606/196 |
| 1250307 | 8/1986 | U.S.S.R. | 128/207.18 |
| 1255128 | 9/1986 | U.S.S.R. | 128/207.18 |
| WO8203548 | 10/1982 | WIPO | A61F 5/56 |
| 9220392 | 11/1992 | WIPO | A61M 16/00 |

OTHER PUBLICATIONS

"Management of Chronic Alveolar Hyperventilation with Nasal Positive Pressure Breathing"; DiMarco, et al; Chest: 92/5/952–954 Nov. 1987.

Benefit of Nasal CPAP in Obstructive Sleep Apnea is Due to Positive Pharyngeal Pressure; N.C. Abbey, K.R. Cooper and J.A. Kwentus; Sleep 12(5) 420–422 (1989).

(List continued on next page.)

Primary Examiner—Vincent Millin
Assistant Examiner—V. Srivastava

[57] ABSTRACT

A nasal positive airway pressure mask is provided having a variable orifice venting aperture member. The variable orifice venting aperture member preferably is mounted to the mask frame, but may be mounted at other locations. The variable orifice vent aperture member expands under increased pressure, e.g., during exhalation, and contracts to its original diameter at lower pressures, e.g., during inhalation, to provide variable venting capacity during positive airway pressure treatment.

18 Claims, 4 Drawing Sheets

U.S. PATENT DOCUMENTS

| | | | |
|---|---|---|---|
| 1,632,449 | 6/1927 | McKesson | 128/207.13 |
| 2,185,997 | 1/1940 | Heidbrink | 128/204.22 |
| 2,245,969 | 6/1941 | Francisco | 128/207.18 |
| 2,259,817 | 10/1941 | Hawkins | 128/207.18 |
| 2,493,326 | 1/1950 | Trinder | 128/325 |
| 2,820,651 | 1/1958 | Phillips | 128/204.18 |
| 2,931,358 | 4/1960 | Sheridan | 128/207.18 |
| 3,481,339 | 12/1969 | Puig | 128/207.14 |
| 3,516,407 | 6/1970 | Ruggero | 128/325 |
| 3,566,862 | 3/1971 | Schuh | 128/207.18 |
| 3,568,678 | 3/1971 | Pourquier | 128/348 |
| 3,640,282 | 2/1972 | Kamen | 128/351 |
| 3,683,907 | 8/1972 | Cotabish | 128/208.28 |
| 3,707,151 | 12/1972 | Jackson | 128/351 |
| 3,766,924 | 10/1973 | Pidgeon | 128/325 |
| 3,794,036 | 2/1974 | Carroll | 128/207.18 |
| 3,850,176 | 11/1974 | Gottschalk | 128/325 |
| 3,856,051 | 12/1974 | Bain | 138/114 |
| 3,903,893 | 9/1975 | Scheer | 128/325 |
| 4,056,104 | 11/1977 | Jaffe | 128/351 |
| 4,090,518 | 5/1978 | Elam | 128/207.18 |
| 4,106,505 | 8/1978 | Salter | 128/207.18 |
| 4,151,843 | 5/1979 | Brekke | 128/204.18 |
| 4,156,426 | 5/1979 | Gold | 128/207.18 |
| 4,178,937 | 12/1979 | Taylor | 128/349 |
| 4,216,769 | 8/1980 | Grimes | 128/207.13 |
| 4,235,239 | 11/1980 | Elam | 128/207.15 |
| 4,273,124 | 6/1981 | Zimmerman | 128/207.18 |
| 4,367,735 | 1/1983 | Dali | 128/207.18 |
| 4,422,456 | 12/1983 | Tiep | 128/207.18 |
| 4,465,067 | 8/1984 | Koch | 128/207.18 |
| 4,538,606 | 9/1985 | Whited | 128/207.15 |
| 4,655,213 | 4/1987 | Rapoport et al. | 128/205.25 |
| 4,753,233 | 6/1988 | Grimes | 128/207.18 |
| 4,782,832 | 11/1988 | Trimble | 128/207.18 |
| 4,790,308 | 12/1988 | Weichselbaum | 128/207.18 |
| 4,818,320 | 4/1989 | Weichselbaum | 128/207.18 |
| 4,836,200 | 6/1989 | Clark | 128/207.18 |
| 4,915,105 | 4/1990 | Lee | 128/205.27 |
| 5,024,220 | 6/1991 | Holmgreen et al. | 128/207.14 |
| 5,036,743 | 8/1991 | Schreurs | 128/205.24 |
| 5,042,478 | 8/1991 | Kopala | 128/207.18 |
| 5,065,756 | 11/1991 | Rapoport | 128/204.18 |
| 5,105,807 | 4/1992 | Kahn et al. | 128/207.18 |
| 5,117,819 | 6/1992 | Servidio et al. | 128/204.18 |
| 5,139,510 | 8/1992 | Goldsmith, III et al. | 606/196 |
| 5,148,802 | 9/1992 | Sanders et al. | 128/204.18 |
| 5,161,525 | 11/1992 | Kimm et al. | 128/204.26 |
| 5,199,424 | 4/1993 | Sullivan et al. | 128/204.18 |
| 5,243,971 | 9/1993 | Sullivan et al. | 128/204.18 |
| 5,245,995 | 9/1993 | Sullivan et al. | 128/204.23 |
| 5,269,296 | 12/1993 | Landis | 128/207.18 |
| 5,477,852 | 12/1995 | Landis et al. | 128/207.18 |

OTHER PUBLICATIONS

Long-Term Compliance with Nasal Continuous Positive Airway Pressure Therapy of Obstructive Sleep Apnea; R.E. Waldhorn, T.W. Herrick, M.C. Nguyen, A.E. O'Donnell, J. Sodero, and S.J. Potolicchio; Chest 1990; 97:33–38.

Obstructive Sleep Apnea Treated by Independently Adjusted Ispiratory and Expiratory Positive Airway Pressures via Nasal Mask; M.H. Sanders, N. Kern; Chest 1990; 98:317–24.

Surgical Treatment of Obstructive Sleep Apnea: Is Mandibular Surgery an Advance?; Chest 1990; 98:1315–16.

Maxillofacial Surgery and Nasal CPAP: A Comparison of Treatment for Obstructive Sleep Apnea Syndrom; R.W. Riley, N.B. Powell and C. Guilleminault; Chest 1990; 98:1421–25.

The Effect of Nightly Nasal CPAP Treatment on Underlying Obstructive Sleep Apnea and Pharyngeal Size; N.A. Collop, A.J. Block and D. Hellard; Chest 1991; 99:855–60.

The Effect of Positive Reinforcement on Hourly Compliance in Nasal Continuous Positive Airway Pressure Users with Obstructive Sleep Apnea; E.C. Fletcher and R.A. Luckett; Am. Rev. Respir. Dis. 1991; 143:936–941.

Nasal Continuous Positive Airway Pressure Facilities Respiratory Muscle Function During Sleep in Severe Chronic Obstructive Pulmonary Disease; B.J. Petrof, R.J. Kimoff, R.D. Levy, M.G. Cosio and S.B. Gottfried; Am. Rev. Respir. Dis. 1991; 143:928–935.

Efficacy of Nocturnal Nasal Ventilation in Patients with Restrictive Thoracic Disease; N.S. Hill, S.E. Eveloff, C.C. Carlisle and S.G. Goff; Am. Rev. Respir. Dis. 1992; 145:365–371.

Nocturnal Nasal Intermittent Positive Pressure Ventilation with Bi-Level Positive Airway Pressure (BiPAP) in Respiratory Failure; R.E. Waldhorn; Chest 1992; 101:516–521.

Physiologic Evaluation of Pressure Support Ventilation by Nasal Mask in Patients with Stable COPD; Chest 1992; 101:385–91.

"Softwear™ Nasal Mask"; Lifecare; ©1991.

New Product News–Companion 318 Nasal CPAP System from Puritan–Bennett.

Harmonization and the Work of Breathing: For Bi-Level Respiratory Therapy; Puritan–Bennett.

Companion® Adam Nasal CPAP Circuit.

New Mask Fitting Program for Health Care Professionals; Night Times; Jun. 1993.

The BiPap® System Compensates for Leaks; Respironics, Inc., ©1993.

Why Mask Leaks Are No Longer a Problem; Respironics, Inc., ©1993.

"The Sullivan™ Mask System" (undated).

NASAL POSITIVE AIRWAY PRESSURE MASK AND METHOD

TECHNICAL FIELD

The present invention relates to an apparatus and method for treating sleep apnea. More specifically, the present invention provides a nasal positive airway pressure mask having a variable orifice vent aperture.

BACKGROUND OF THE INVENTION

Obstructive sleep apnea is a condition in which the patient's airway passage is blocked and no air can pass to the lungs during sleep. During a customary sleep period a person suffering from sleep apnea can experience so-called apneic events. Apneic events are periods when the patient's airway becomes blocked, often for ten seconds or more, until the patient rouses from sleep and starts breathing normally again. Those suffering from sleep apnea may experience numerous apneatic events each night, causing a deficiency of restful sleep and, due to depleted oxygen levels, possible long term health problems such as heart ailments.

Continuous positive airway pressure (CPAP) and, more specifically, nasal continuous positive airway pressure (nCPAP) has been shown to be an effective treatment for sleep apnea. See "Benefit of Nasal CPAP in Obstructive Sleep Apnea is Due to Positive Pharyngeal Pressure", N. C. Abbey, K. R. Cooper and J. A. Kwentus, Sleep 1989, 12 (5):420–422; "The Effect of Nightly Nasal CPAP Treatment on Underlying Obstructive Sleep Apnea and Pharyngeal Size", N. A. Collopp. A. J. Block and D. Hellard, Chest 1991, 99:855–860; and "Nasal Continuous Positive Airway Pressure Facilitates Respiratory Muscle Function During Sleep in Severe Chronic Obstructive Pulmonary Disease", B. J. Petrof, R. J. Kimoff, R. D. Levy, M. G. Cosoi and S. B. Gottfried, Am. Rev. Respir. Dis. 1991; 143:928–935. This treatment involves applying a constant supply of gas, typically a mixture of air supplemented with moisture vapor or oxygen, to the nasal passages at a predetermined, slightly elevated pressure in order to prevent negative pressure conditions within the passageway.

More recently, a related form of treatment has been tested and may achieve success similar to nCPAP. In this treatment, known as BiPAP™ therapy, a controller regulates the gas pressure in response to the patient's breathing patterns and supplies positive gas pressure at a first gas pressure during the inspiratory phase, i.e., inhalation by the patient, and supplies gas at a second, reduced pressure during the expiratory phase, i.e., as the patient exhales. The first gas pressure typically corresponds to pressure used in nCPAP treatment, and is on the order of about 10 centimeters of water or greater. The second pressure level is about half the first gas pressure, and typically is about 5 to 7 centimeters of water pressure. It has been reported that reducing the gas pressure during exhalation provides increased patient comfort and compliance by reducing the work done by the patient in overcoming the gas pressure during exhalation. BiPAP™ treatment is disclosed in "Obstructive Sleep Apnea Treated by Independently Adjusted Inspiratory and Expiratory Positive Airway Pressures via Nasal Mask", M. H. Sanders and N. Kern, Chest 1990; 98:317–24; "Nocturnal Nasal Intermittent Positive Pressure Ventilation with Bi-level Positive Airway Pressure (BiPAP) in Respiratory Failure", R. E. Waldhorn, Chest 1992, 101:16–521; "Efficacy of Nocturnal Nasal in Patients with Restrictive Thoracic Disease", Am. Rev. Respir. Disease, 1992; 145:365–371; "Physiologic Evaluation of Pressure Support Ventilation by nasal mask in Patients With Stable COPD", N. Ambrosino, S. Nava, P Bertone, C. Frachia, C. Rampulla, Chest 1992; 101: 385–91. As will be appreciated, BiPAP™ treatment requires sensing and control mechanisms to monitor and adjust treatment gas pressure.

In general, nCPAP and BiPAP™ treatment typically involve placing a mask over the nose of the patient by means of a harness or other headgear and providing a source of positive low pressure air connected to the mask. One such mask is the Sullivan Bubble Mask, available from ResCare, Inc., San Diego, Calif.

U.S. Pat. No. 4,782,832 issued to Trimble, et. al. proposes a device for nCPAP treatment intended as an alternative to conventional mask devices. The Trimble structure has become the accepted apparatus for nCPAP treatment. Trimble discloses a nasal puff adapted to be worn adjacent the nose of the wearer-patient. The nasal device includes a relatively small plenum chamber including structure defining an inlet adapted for coupling with a source of gas, and a pair of spaced apart, separate gas outlets in communication with the inlet. Typically, the plenum chamber is in the form of a generally Y-shaped hollow body with the gas outlets located in the branches of the body. The nasal puff further includes a pair of gas delivery elements each having a gas flow passageway therethrough and respectively operatively coupled with a corresponding gas outlet for conveying gas from the outlet through and out the passageway. Each of the gas delivery elements is configured for insertion into a respective naris of a patient, and for this purpose the outer wall of the elements are generally frustoconically shaped so as to sealingly engage the naris-defining surfaces of the nose. Adjustability of the naris elements is provided by rotatably mounting the elements to the plenum housing and by mounting the elements in slots permitting selective lateral positioning of the elements with respect to each other. Flexible bellows-type corrugated sections can be provided in each of the elements and/or in appropriate positions in the plenum housing so as to add further ranges of flexibility and adjustability. The nares elements are fabricated from relatively soft, deformable, shape-retaining synthetic resin material permitting manual deformation and alteration of the effective shape and position of the elements. Trimble discloses a harness to be worn on a patient's head with flexible retaining straps extending from the main harness strap to each side of the nasal puff. The harness assembly includes an elongated gas-conveying tube which is adapted for coupling with the inlet of the nasal puff and extends upwardly along the length of the bridge of the patient's nose and across the patient's forehead, terminating at the top of the patient's forehead. The tube is longitudinally bifurcated to divide the overall tube and present a pair of elongated, juxtaposed passageways, one of which is connected to a source of pressurized air and the other to a discharge tube for purging patient-generated $CO_2$ during exhalation). In an alternative embodiment Trimble discloses inflatable nares elements that are inserted into the nares and inflated manually by a separate source of pressure.

The Trimble nasal puff and harness assembly is an accepted apparatus for treatment of sleep apnea using nCPAP therapy. While the Trimble device is an improvement over prior mask structures, some patients continue to object to the Trimble structure as uncomfortable to wear. Studies show that a small but significant number of patients fail or are unable to continue nCPAP treatment due in at least some cases to the inconvenience or discomfort of wearing the presently available apparatus. See "The Effect of Positive Reinforcement on Hourly Compliance in Nasal Continuous Positive Airway Pressure Users with Obstructive Sleep Apnea", E. C. Fletcher and R. A. Luckett, Am. Rev. Respir. Dis. 1991; 143:936–941; "Maxillofacial Surgery and Nasal CPAP", R. W. Riley, N. B. Powell, C. Guilleminault, Chest 1990; 98:1421–1425; and "Surgical Treatment of Obstructive Sleep Apnea—Is Mandibular Surgery an Advance?", Chest 1990; 98:1315–1316.

U.S. Pat. No. 5,269,296 to Landis discloses and claims a nasal airway pressure device having a pair of cannulae. Each cannula has an inflatable cuff in gaseous communication with the cannula lumen such that the cuff is inflated during use to gently but securely position the cannula relative to the sensitive nares walls. The Landis 296 patent also discloses vent holes adjacent the cannulae for relieving excess gas pressure created during exhalation.

U.S. Pat. No. 5,477,852 to Landis and Disanza discloses and claims a nasal airway pressure device including a variable orifice vent hole.

A mask having a valve is proposed in Rapoport U.S. Pat. Nos. 4,655,213 and 5,065,756. A mask with a flap valve is shown in Bolton U.S. Pat. No. 1,158,780.

Notwithstanding the general consensus that nasal positive airway pressure is an effective treatment for sleep apnea, a substantial number of patients either cannot tolerate treatment or choose to forego treatment. It is believed a substantial number of such patients could benefit from a nasal positive airway pressure apparatus which is more convenient to use and comfortable to wear, thereby resulting in increased treatment compliance. The device disclosed and claimed herein may find application to either nCPAP or BiPAP treatment.

SUMMARY OF THE DISCLOSURE

In accordance with the present disclosure, a positive nasal airway pressure mask is provided for treatment of sleep apnea. The device includes means for securing the mask to the patient's head, i.e., a head strap or harness, a primary air tube to be connected to a source of air pressure in a known manner, and a nasal mask to deliver pressurized air to the nose of the patient. In accordance with the disclosure, the nasal mask is improved by associating one or more variable orifice members with the nasal mask. The variable orifice member(s) respond to increased air pressure within the mask at various stages of operation, e.g., exhalation, to relieve excess pressure. Variable pressure relief may provide increased patient comfort and, hence, greater patient compliance. Preferably, the variable orifice member is an elastic membrane having an aperture. The membrane stretches in response to increased gas pressure, and the aperture increases in size as the membrane stretches. The membrane and aperture return to their original configuration when the gas pressure subsides.

In use, the mask is secured to the head of the user with the securing strap or harness and the mask is positioned over the patient's nose in substantially sealing engagement with the patient's face. The source of pressurized air is activated to supply pressurized air to the mask via a conduit attached to an inlet port of the mask. The pressurized air passes through the mask and enters the patient's nostrils to effect treatment. Excess gas pressure within the mask typically is not a problem during inhalation. As the patient exhales, however, excess gas pressure can build up in the mask and contribute to patient discomfort and, hence, noncompliance.

In accordance with the disclosure, excess pressure within the mask is vented through the variable orifice vent hole(s) associated with the mask. Because the variable orifice is constructed of an elastic material, the orifice material expands in response to increased gas pressure within the device, thereby increasing the area of the vent orifice hole and temporarily increasing the venting capacity of the orifice. As gas pressure within the device subsides, e.g., as inhalation commences, the elastic material returns to its original configuration with a smaller orifice area or diameter. In this manner, the venting capacity of the variable orifice vent aperture increases during exhalation or under other increased pressure conditions to relieve excess pressure, and returns to its original, reduced aperture size and venting capacity when such increased venting capacity is not required, e.g., during normal inhalation with pressurized gas supplied to the nose. Thus, excess pressure within the device, as may occur during exhalation, can promptly and effectively be relieved, while permitting optimum direction of pressurized air to the nose under normal operating pressure conditions, e.g., inhalation. Because excess gas pressure can contribute to patient discomfort and noncompliance, the effectiveness of treatment may be increased.

The apparatus in accordance with the disclosure provides considerable advantages over existing treatment devices by providing a device which is more comfortable to use. Moreover, because the variable orifice vent aperture automatically adjusts the venting capacity of the device in response to increasing and decreasing pressure within the device, e.g., during inhalation and exhalation, it may be possible to achieve results comparable to BiPAP™ with a simple mechanical device and continuous positive pressure, without complex air pressure monitoring and control systems. These and other advantages of the invention will become apparent to those skilled in the art from the foregoing general description and the following detailed disclosure, and from practice with the devices constructed in accordance with the disclosure.

BRIEF DESCRIPTION OF THE DRAWINGS

The disclosure set forth herein can be better understood with reference to the accompanying drawings, which form a part of the disclosure, in which.

Figure 1:
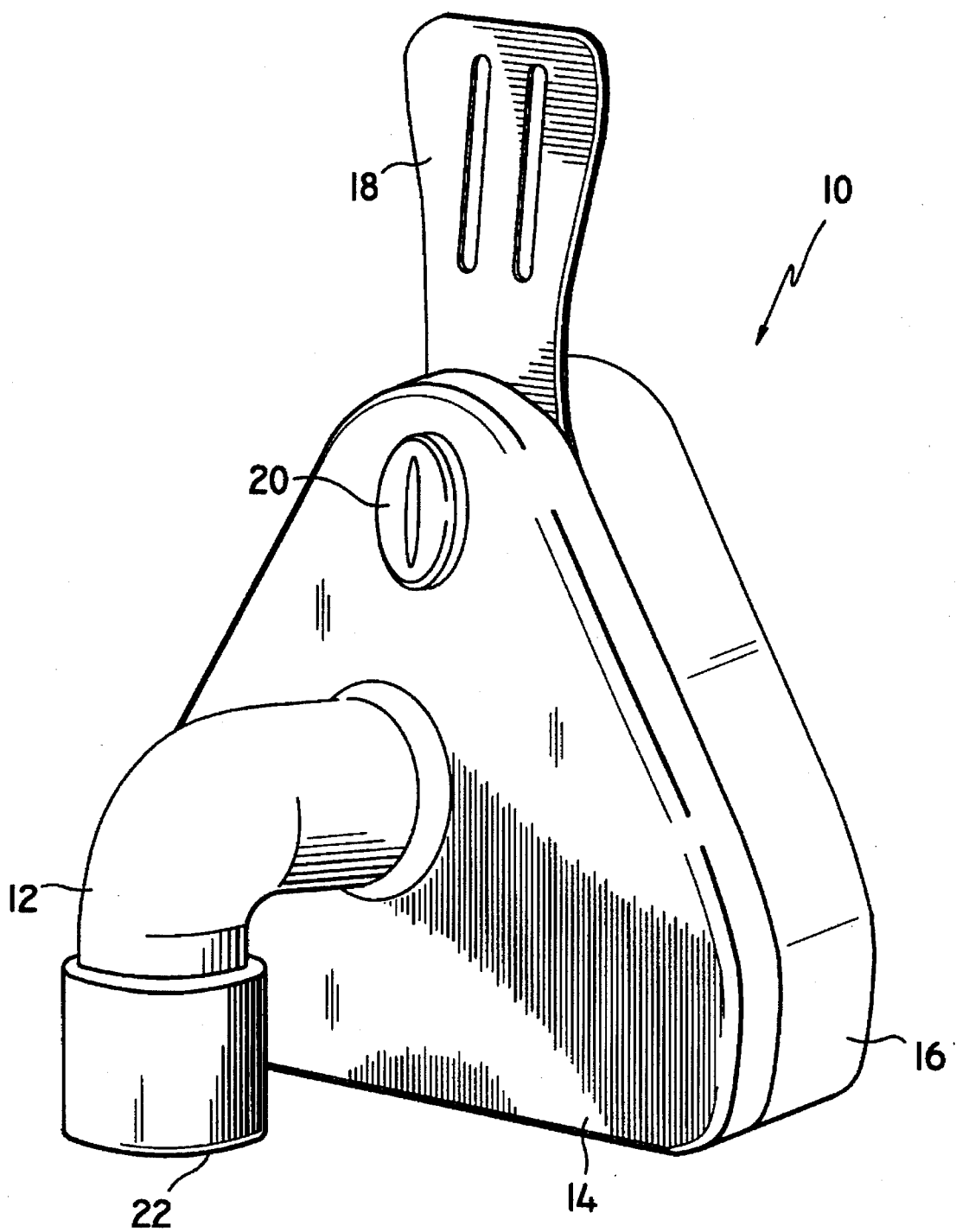
FIG. 1 is a front perspective view of a mask in accordance with the disclosure.

As those skilled in the art will appreciate, the foregoing drawings are illustrative only, and show the features of the invention in accordance with the disclosure as they relate to one another. The drawings are not drawn strictly to scale and should be interpreted accordingly.

DETAILED DESCRIPTION OF THE PREFERRED EMBODIMENTS

Referring generally to the drawings, wherein common reference numerals are used to refer to like elements, there is shown a nasal mask 10. Mask 10 generally consists of an air tube connector 12, a mask frame 14, a compliant face engaging mask portion 16, and means 18 for securing the mask to a patient's head, and a variable orifice member 20. The apparatus may be secured to the head of the user in a known manner, such as by a head band. As will be explained in greater detail below, in use the nasal mask is mounted over the patient's nose to deliver pressurized air to effect treatment.

FIG. 1 is a front perspective view of a mask constructed in accordance with the disclosure. Air tube connector 12 preferably is made of a suitable medical grade plastic material with sufficient rigidity to retain its shape during use. Air tube connector 12 has an inlet port 22 configured to be connected to a source of pressurized gas, such as by a flexible air tube connected, in turn, to a source of pressurized air in a known manner. The source of pressurized gas may be any source suitable for treating sleep apnea, and may be a source of pressurize air with or without supplements such as oxygen. The source of gas may provide continuous pressure as used in nCPAP treatment, or may provide varied levels of pressure such as used in BiPAP™ treatment. In either case, the maximum gas pressure typically is in the range of about 5 to about 15 centimeters of water.

Air tube connector 12 is connected in sealing engagement to mask frame 14. Preferably, air tube connector 12 is rotatably mounted to the mask frame for adjustability. Most preferably, air tube connector 12 also is rotatably connected to an air tube at inlet port 22 to provide maximum adjustability between the air tube and the mask. Mask frame 14 is substantially rigid to provide support for the air tube connector and the face engaging mask portion 16. Mask frame 14 may be of any suitable plastic or metal material to provide such support, and has apertures to receive air tube connector 12 and variable orifice member 20. Preferably, the aperture in mask frame 14 to receive variable orifice member 20 is configured as a cylindrical wall projecting outward from the mask frame to engage a variable orifice member cap, as described in greater detail below. The means 18 for securing the mask to a patient's head is attached to mask frame 14. As shown, means 18 may be a head strap holder and a head band or strap. Alternative devices are also contemplated, such as a harness or plurality of strap engaging members disposed at various positions on the mask. Accordingly, as used herein, "means for securing the mask to a patient's head" is broadly intended to include all of the foregoing structures, equivalent structures, and all other suitable structures for mounting the mask to the patient's head. Also attached to mask frame 14 is face engaging mask portion 16. Face engaging mask portion 16 preferably is made of a soft synthetic material which is comfortable to wear in contact with the face, and which can form a substantially airtight seal to the face around the nose. One suitable material is a soft, medical grade silicone. The face engaging portion is sealingly mounted to the mask frame by any suitable method, such as by gluing, welding, lip seal frictional engagement, etc.

Figure 2:
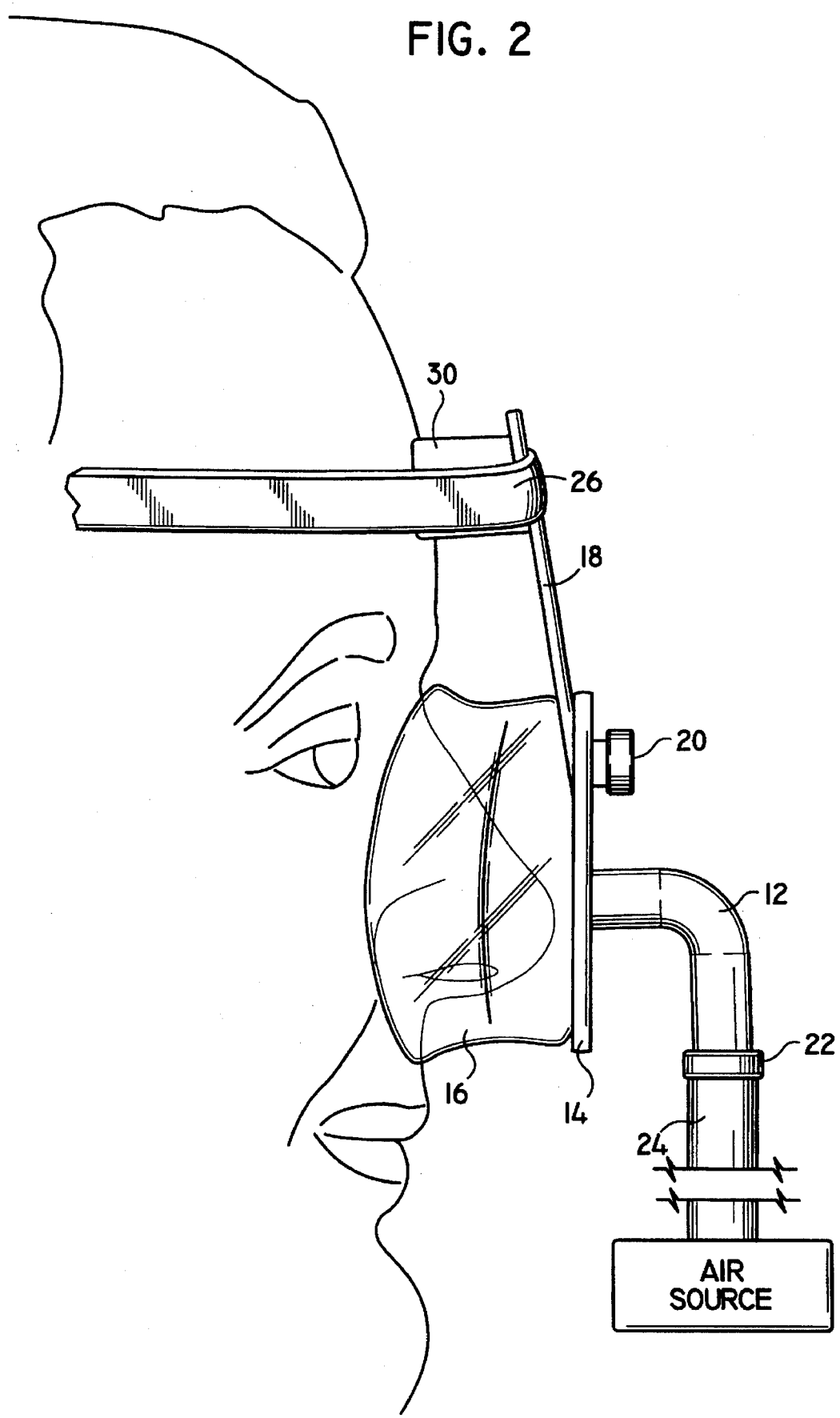
FIG. 2 is a side view of the mask of FIG. 1 mounted upon the head of a patient.
Figure 3:
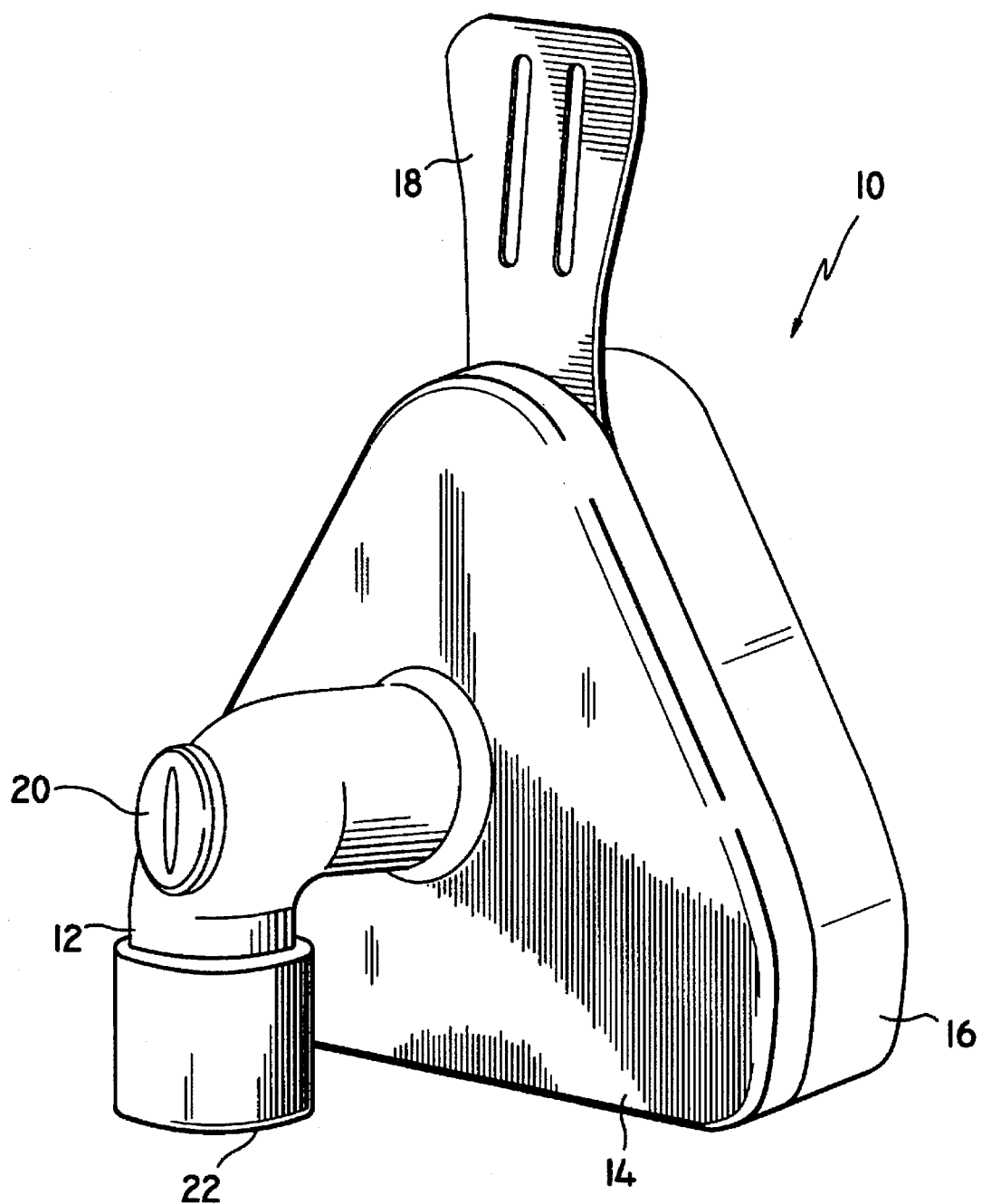
FIG. 3 is a perspective view of a mask in accordance with the disclosure with the variable orifice member mounted to the air conduit.

Referring now to FIG. 2, a side view of the mask of FIG. 1 mounted to a patient's face, the air tube connector is connected to an air tube 24 at inlet port 22. Air tube 24 is, in turn, connected to a source of pressurized air, as schematically illustrated in FIG. 2. A head band 26 holds the device in place relative to the user's head, preferably by engaging the strap holder attached to the mask frame. As shown, a foam or other cushioned pad 30 may be placed between the strap holder and the forehead of the user for added comfort. As will be appreciated, pad 30 may be pre-attached to the strap holder for ease of use. Headband 26 preferably is a cloth or plastic strap with a simple fastening structure such as a hook and loop fastener, e.g., a Velcro™ fastener. As shown in FIGS. 1 and 2, and described in greater detail below, a variable orifice member 20 is provided on the mask. As shown in FIGS. 1 and 2, variable orifice member 20 preferably is mounted to the mask frame. FIG. 3 is a front perspective view of an alternative configuration wherein the variable orifice member 20 is mounted to the air tube connector 12.

As shown throughout the figures, the device includes a variable orifice vent aperture member 20. Variable orifice vent aperture member 20 preferably is mounted to the mask frame, as shown in FIGS. 1–2, although it is contemplated that the variable orifice member may be mounted to the primary tube, nasal tube, or other similar conduits or connectors adjacent the patient's nose. One such configuration is illustrated in FIG. 3, wherein the variable orifice member is mounted to the air tube connector. In one construction, variable orifice vent aperture member 20 is configured as a cap to mount onto and engage projecting walls of a cylindrical opening in the mask frame or other associated structure (not shown). This is just one method of mounting the variable orifice vent aperture member to the device, and other structures and methods will occur to those skilled in the art with practice.

Figure 4A:
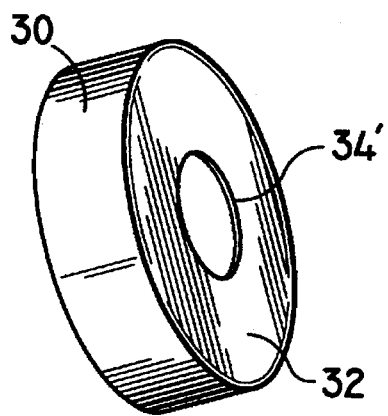
FIG. 4A is a perspective view of a variable orifice cap illustrating the orifice defining surface in the first, unexpanded condition to provide a first aperture diameter.
Figure 4B:
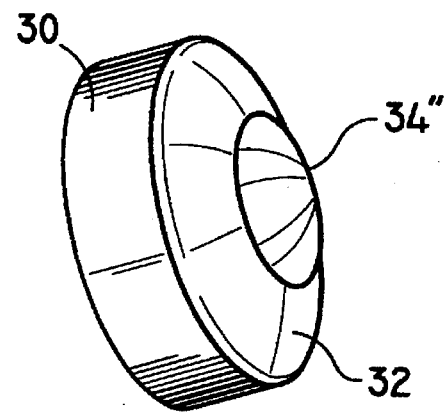
FIG. 4B is a perspective view of the variable orifice cap of FIG. 4A, illustrating the orifice defining surface in a second, expanded condition to provide a second, enlarged aperture diameter.
Figure 4C:
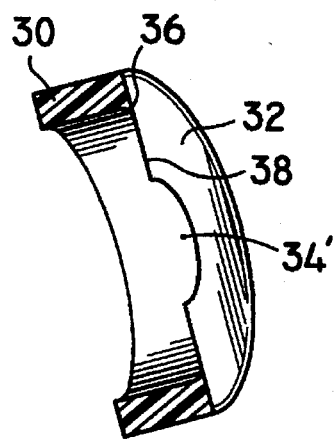
FIG. 4C is a sectional view, in perspective, of the variable orifice cap of FIG. 4A.
Figure 4D:
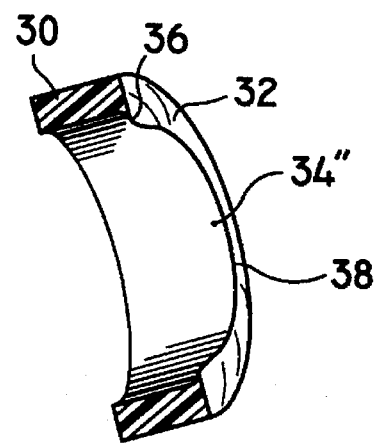
FIG. 4D is a sectional view, in perspective, of the variable orifice cap of FIG. 4B.

Referring now to FIGS. 4A–4D, the variable orifice cap 20 is shown in greater detail. FIG. 4A is a perspective view of the variable orifice cap having vertical side walls 30 and an aperture defining surface 32. The variable orifice cap is shown in FIG. 4A in the first, unexpanded state defining aperture 34' having a first, reduced diameter. Referring now to FIG. 4B, aperture defining surface 32 is shown in a second, expanded state defining an expanded aperture 34" having a second diameter which is larger than the diameter of 34'. FIG. 4C is a perspective sectional view of the variable orifice cap of FIG. 4A shown in the unexpanded state. As shown, side walls 30 have a first thickness sufficient to give rigidity to the cap and frictionally engage a cylindrical projecting wall on the device. Aperture defining surface 32 is of substantially reduced thickness compared to side wall 30, and may taper from a first thickness at a point 36 adjacent side wall 30 to a very thin, flexible thickness 38 immediately adjacent aperture 34'. Referring now to FIG. 4D, a perspective section view of the variable orifice cap of FIG. 4B showing aperture defining surface 32 in the expanded state, the aperture defining surface 32 is expanded in the area adjacent the aperture to define larger expanded aperture 34". More particularly, the reduced thickness portion 38 of surface 32 stretches under pressure to expand the diameter of the aperture. At least the aperture defining surface 32 of variable orifice cap 20 is made of a flexible material capable of expanding and contracting, such as latex rubber.

In use, the variable orifice cap is mounted over and onto the projecting wall of the mask. The mask is placed against the patient's face over the nose and the source of pressurized air is activated. During inhalation the pressure at the orifice cap is at a minimum level and the aperture defining surface 32 is in the unexpanded state shown in FIGS. 4A, 4C. During exhalation the gas pressure at orifice cap increases and exerts pressure upon orifice defining surface 32 to cause the surface to stretch and expand, creating expanded orifice 34" as shown in FIGS. 4B and 4D. The variable orifice cap is an improvement over fixed aperture devices because the first, unexpanded aperture state allows efficient transfer of pressurized gas to the nose of the patient at relatively low pressure during inhalation. Conversely, during exhalation the gas pressure adjacent variable orifice cap substantially increases and the increased pressure causes orifice defining surface 32 to stretch and expand, resulting in the aperture assuming a larger diameter expanded state. This allows more exhaled gas to exit the device through the aperture than a fixed orifice device, which typically has an opening on the order of the unexpanded state of the variable orifice. With a fixed orifice device much of the exhaled gas backs up into the source tube, and may be re-inhaled by the patient during subsequent inhalation. Advantageously, the variable orifice cap may be used with any form of positive nasal airway pressure therapy, e.g. nCPAP or BiPAP™ therapy.

Of course, numerous modifications and alterations to the variable orifice will occur to those skilled in the art. By way of example only, the stretchable orifice defining surface could be mounted to the mask in a variety of ways, such as by mounting the stretchable membrane directly to a surface of the device across an opening, such as by gluing a latex rubber membrane defining the variable orifice to an inside surface of the mask over an opening. Similarly, a substantially flat variable orifice defining member could be placed over aperture 34, with a substantially rigid open-centered cap placed over the orifice defining member to capture the orifice defining member under the cap. In addition, it will be understood that the variable orifice member can be positioned at other locations than shown in the FIGS., as long as the variable orifice member is placed reasonably close to the patient's nose along the path of the gas supply. These and other modifications will occur to those skilled in the art after learning of and practicing the apparatus disclosed herein.

The device may be fabricated in whole or in part from disposable or reusable plastics such as ABS plastic, polystyrene, polyethylene terathalate, polycarbonate, polyurethanes, polyesters, polypropylene, polyethylene, acrylics, steel, aluminum, titanium, tantalum, alloys of the foregoing, etc. and may be fabricated by any suitable techniques such as blow or injection molding, extrusion, grinding, cutting, etc. The entire device may be disposable, or only parts of the instrument may be disposable. For example, all parts other than the face engaging portion of the mask might be relatively permanent with only the face engaging portion being periodically replaced.

The foregoing description contains many specifics and numerous alternative structures and combinations will occur to those skilled in the art. As previously stated, for example, it is contemplated that a plurality of variable orifice members may be provided at various locations on the device to achieve substantially the same results. These and numerous other changes, variations and improvements will occur to those skilled in the art with practice of the invention claimed in the accompanying claims.

What is claimed is:

1. A device for treatment of sleep apnea comprising:
    a source of pressurized air;
    a nasal mask in communication with the source of pressurized air, the nasal mask being configured and dimensioned to cover the nose of a patient in substantial sealing engagement with the patient's face, and to deliver pressurized air from the source to the nose of a patient;
    at least one variable orifice member defining a variable orifice which assumes a first position having a first diameter at a first gas pressure and a second, expanded position having a second diameter greater than said first diameter at a second, increased gas pressure.

2. The device of claim 1 wherein the mask includes a mask frame and a face engaging portion.

3. The device of claim 1 wherein the mask is connected to the source of pressurized air by a primary air tube.

4. The device of claim 3 wherein the variable orifice member is mounted to the primary air tube.

5. The device of claim 2 wherein the variable orifice member is mounted to the mask frame.

6. The device of claim 2 wherein the face engaging portion is made of a compliant synthetic material.

7. The device of claim 1 wherein the source of pressurized air is a source of substantially constant pressure air.

8. The device of claim 1 wherein the source of pressurized air provides at least two different pressure conditions of air.

9. The device of claim 1 further comprising means for mounting the mask to the head of a patient.

10. The device of claim 1 wherein the variable orifice member comprises a stretchable material having an aperture therethrough.

11. A nasal mask for treatment of sleep apnea comprising:
    a nasal mask configured and dimensioned to cover the nose of a patient in substantial sealing engagement with the patient's face to deliver pressurized air to the nose of a patient;
    at least one variable orifice member mounted to the mask defining a variable orifice which assumes a first position having a first diameter at a first gas pressure and a second, expanded position having a second diameter greater than said first diameter at a second, increased gas pressure.

12. The nasal mask of claim 11 wherein the mask includes a mask frame and a face engaging portion.

13. The nasal mask of claim 12 wherein the variable orifice member is mounted to the mask frame.

14. The nasal mask of claim 12 wherein the face engaging portion is made of a compliant synthetic material.

15. The nasal mask of claim 11 further comprising means for mounting the mask to the head of a patient.

16. The nasal mask of claim 11 wherein the variable orifice member comprises a stretchable material having an aperture therethrough.

17. The nasal mask of claim 16 wherein the stretchable material is an elastic membrane.

18. A method of treating for sleep apnea comprising:
    connecting a source of pressurized air to a nasal mask configured and dimensioned to cover the nose of a patient, the mask further including at least one variable orifice member defining a variable orifice which assumes a first position having a first diameter at a first gas pressure and a second, expanded position having a second diameter greater than said first diameter at a second, increased gas pressure;
    mounting the nasal mask to the face of a patient over the patient's nose in substantial sealing engagement with the patient's face;
    activating the source of pressurized air to supply positive air pressure to the nasal mask, the variable orifice member assuming the first diameter during inhalation by the patient and the second, enlarged diameter during exhalation by the patient.

* * * * *